United States Patent
Basterrechea et al.

(10) Patent No.: US 8,301,220 B2
(45) Date of Patent: Oct. 30, 2012

(54) MEDICAL SYSTEM COMPRISING A DETECTION DEVICE FOR DETECTING AN OBJECT AND COMPRISING A STORAGE DEVICE AND METHOD THEREOF

(75) Inventors: Juan Manuel Casso Basterrechea, Majadahonda (ES); Rainer Kaltschmidt, Eckental/Brand (DE)

(73) Assignee: Siemens Aktiengesellschaft, München (DE)

( * ) Notice: Subject to any disclaimer, the term of this patent is extended or adjusted under 35 U.S.C. 154(b) by 546 days.

(21) Appl. No.: 11/904,413

(22) Filed: Sep. 27, 2007

(65) Prior Publication Data

US 2008/0177176 A1   Jul. 24, 2008

(30) Foreign Application Priority Data

Sep. 27, 2006  (DE) .......................... 10 2006 045 718

(51) Int. Cl.
*A61B 5/05* (2006.01)

(52) U.S. Cl. ........ 600/407; 382/260; 382/261; 382/262; 382/263; 382/264; 382/265; 382/266; 382/267; 382/268; 382/274

(58) Field of Classification Search .................. 600/407; 359/3, 12, 5, 35, 17; 382/154, 128
See application file for complete search history.

(56) References Cited

U.S. PATENT DOCUMENTS

| | | | |
|---|---|---|---|
| 4,675,766 A * | 6/1987 | Schewe ..................... 360/123.11 |
| 4,692,797 A * | 9/1987 | Matsumoto ................... 358/506 |
| 5,276,313 A | 1/1994 | Nakazawa et al. |
| 5,745,406 A * | 4/1998 | Yamane et al. ................ 365/158 |
| 5,963,211 A * | 10/1999 | Oikawa et al. ................ 345/424 |
| 6,312,381 B1* | 11/2001 | Knell et al. .................... 600/437 |
| 2002/0192506 A1* | 12/2002 | Coffey et al. .......... 428/694 TM |
| 2003/0149526 A1* | 8/2003 | Zhou et al. .................... 701/213 |
| 2004/0057623 A1* | 3/2004 | Schuhrke et al. ............. 382/232 |
| 2004/0116797 A1 | 6/2004 | Takahashi et al. |
| 2004/0247175 A1* | 12/2004 | Takano et al. ................. 382/154 |
| 2005/0033176 A1* | 2/2005 | Kawabata et al. ............ 600/454 |
| 2005/0090743 A1* | 4/2005 | Kawashima et al. ......... 600/443 |
| 2006/0020203 A1* | 1/2006 | Tamura ......................... 600/437 |
| 2006/0034427 A1 | 2/2006 | Brooks |
| 2007/0146835 A1* | 6/2007 | Erben et al. ....................... 359/3 |

* cited by examiner

*Primary Examiner* — Tse Chen
*Assistant Examiner* — Joel F Brutus

(57) ABSTRACT

The invention relates to a medical system comprising a detection device for detecting an object in at least two dimensions by x-rays. The detection device is constructed to detect the object and to produce data comprising a 2D data record or a sequence of 2D data records over time representing the object in a projection through the object in two dimensions and to output the data. The medical system comprises at least one storage device with a data input actively connected to the detection device and which is constructed to receive the data at the input side and to write on a storage medium, in particular a portable storage medium, in such a way that the storage medium represents the data so it can be read out again. The medical system is constructed to digitally transmit the data from the detection device through to the storage device.

16 Claims, 1 Drawing Sheet

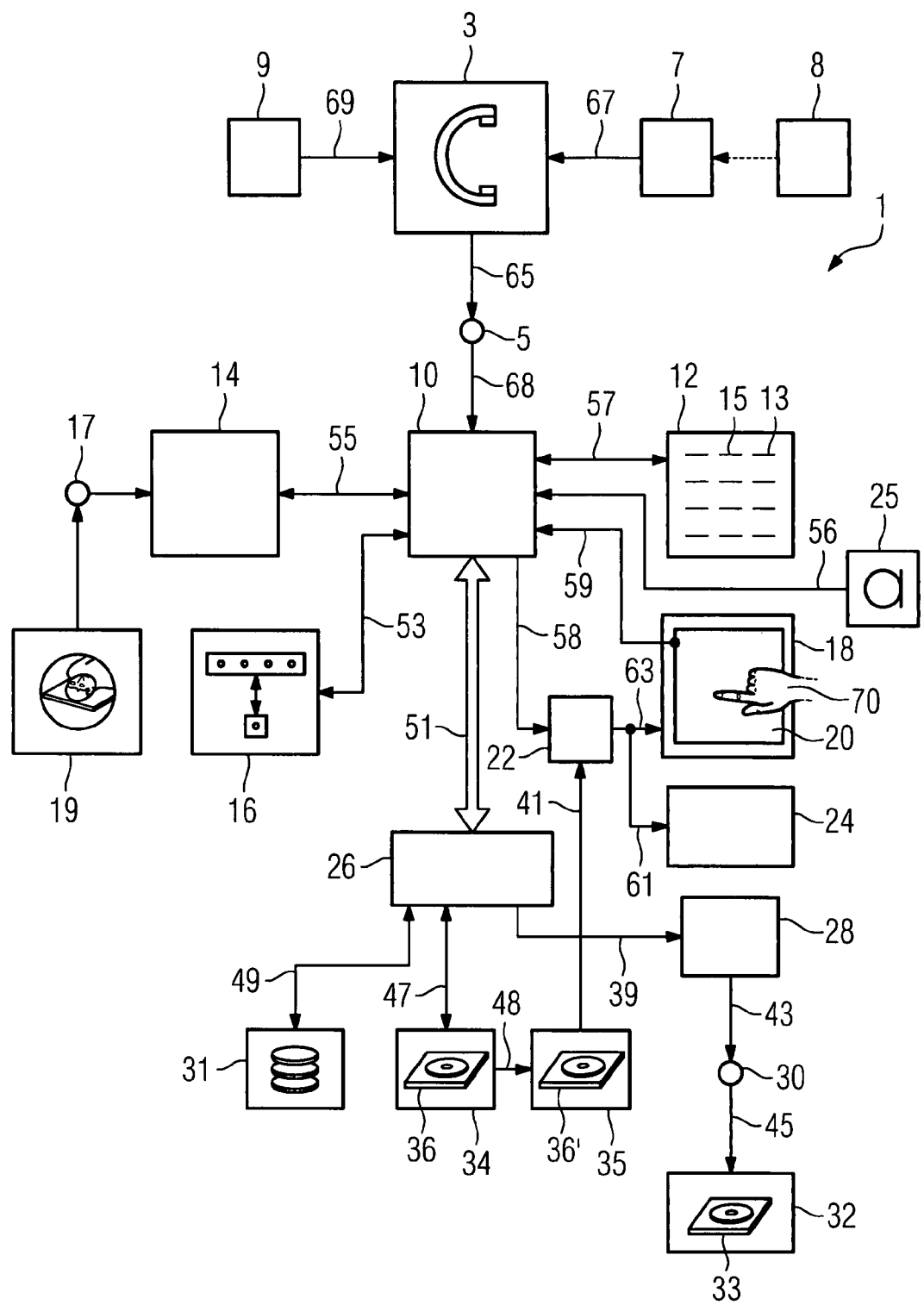

MEDICAL SYSTEM COMPRISING A DETECTION DEVICE FOR DETECTING AN OBJECT AND COMPRISING A STORAGE DEVICE AND METHOD THEREOF

CROSS REFERENCE TO RELATED APPLICATIONS

This application claims priority of German application No. 10 2006 045 718.8 filed Sep. 27, 2006, which is incorporated by reference herein in its entirety.

FIELD OF THE INVENTION

The invention relates to a medical system comprising a detection device for detecting an object in at least two dimensions by means of x-rays and comprising at least one storage device with a data input actively connected to the detection device and a method thereof.

BACKGROUND OF THE INVENTION

In the medical systems known from the prior art a video recorder is known as a storage device with which data produced by a medical device, and representing a detected object, can be stored. It is therefore possible for example to record data produced by an x-ray C-arm device by means of the video recorder. For this purpose an image signal, which has been produced for example by a solid-state detector or a CCD detector (CCD=Charge Coupled Device), is converted by means of a standard converter into a BAS or FBAS signal (BAS=image blanking signal; FBAS=color image blanking signal) which can be recorded by a video recorder or a DVD recorder.

SUMMARY OF THE INVENTION

The object underlying the invention is to disclose a medical system which allows improved storage of detection results of a medical image detection device.

This object is achieved by a medical system comprising a detection device for detecting an object in at least two dimensions by means of x-rays. The detection device is constructed to detect the object in a projection through the object and to produce data comprising at least one 2D data record or a sequence of 2D data records over time, the 2D data record representing the object in a projection through the object in two dimensions and data record representing the object in a projection through the object in two dimensions and the detection device being constructed to output the data at the output. The medical system comprises at least one storage device with a data input actively connected to the detection device and which is constructed to receive the data at the input side and to write on a storage medium, in particular a portable storage medium, in such a way that the storage medium represents the data so it can be read out again. The medical system is constructed to digitally transmit, in particular in a binary, octal or hexadecimal manner, or a combination thereof, data from the detection device through to the storage device. The combination can for example be binary and octal, binary and hexadecimal or octal and hexadecimal.

An original information content of an image signal or image data record can advantageously be obtained and stored without loss of information by a medical system of this kind. A converter for converting an image signal into an analog BAS signal for example reduces a frequency bandwidth of an image signal, corresponding to an information content, so the information content of a converted detection result is also reduced. Detailed information, in particular a spatial resolution, a contrast or color resolution of the image data record, is disadvantageously lost thereby.

In a preferred embodiment the at least one storage device is an optical storage device which is constructed to write on the storage medium by means of electromagnetic beams. The storage device is also preferably constructed to read the storage medium again by means of the electromagnetic beams and to produce data, in particular a 2D data record, which represents the data stored on the storage medium, in particular the 2D data record. This kind of optical storage, in particular digital optical storage, makes lossless or low-loss storage of data possible.

In a preferred embodiment the optical storage device is a compact disc storage device or a DVD storage device (DVD=Digital Versatile Disc). Preferred embodiments for a DVD storage device are an HD-DVD storage device (HD-DVD=High Density Digital Versatile Disc) or a Blu-ray DVD, which in each case are constructed to write on the storage medium by means of electromagnetic beams produced by a laser, in the wavelength range between 380 and 420 nanometers, preferably 405 nanometers. A higher data density can advantageously be achieved on a storage medium by a storage device with a laser which can produce electromagnetic beams with a wavelength of 405 nanometers.

In an exemplary embodiment for a storage medium, in particular a DVD disc, the storage medium can store up to 27 gigabytes.

In a further embodiment the storage device is constructed to advantageously write on DVD discs with at least two storage layers, the storage layers are preferably arranged parallel to each other respectively. A storage capacity of a storage medium can thus advantageously be increased. Storage media with two, three, four or up to ten storage layers are conceivable.

An optical storage device is advantageously constructed for writing on a (+R) storage medium and/or a (−R) storage medium.

In a further advantageous variant the storage device is an HVD storage device (HVD=Holographic Versatile Disc). The HVD storage device is constructed to write on a holographic storage medium, comprising a substrate layer, in particular polycarbon layer, a photopolymeric data carrier layer, distance layers, a dichroitic layer reflecting green light, an aluminum layer reflecting red light, and a transparent base by means of a green write/read laser, emitting electromagnetic beams in the range between 480 and 550 nanometers, preferably 532 nanometers, and a second red positioning and addressing laser, emitting electromagnetic beams in the range between 600 and 800 nanometers, preferably 650 nanometers, and reading out again information written thereon. A multi-layer storage system, which comprises a storage layer for storing positioning and addressing information, and at least one further storage layer for storing coding information, may advantageously produce an increased bit density. The dichroitic later mentioned in advance, which is arranged between holographic data and auxiliary data reflects the electromagnetic radiation of the blue-green laser at a wavelength of 532 nanometers and allows the electromagnetic radiation of the red laser through. An indifference of the auxiliary data, produced by refraction of the blue-green electromagnetic radiation, is thus advantageously prevented. A storage capacity of up to one terabyte may advantageously be produced by an HVD storage device in connection with an HVD storage disc. A read/write rate can advantageously be up to one gigabyte per second.

In an advantageous embodiment the optical storage device is a magnetic-optical disc storage device which is constructed to optically read and magnetically write on a storage medium, in particular a rotating, disc-like storage medium. A Kerr effect of magnetic-optical material, contained by the storage medium, is advantageously utilized in a MOD storage device of this kind. An MOD storage device of this kind, in connection with a corresponding MOD storage medium, has the advantage that the MOD storage medium can be multiply deleted and rewritten.

In a preferred embodiment of the medical system at least one storage device is a magnetic storage device which is constructed to produce a magnetic field and to write on the storage medium by means of the magnetic field. A magnetic storage device of this kind is for example a hard disc which comprises at least one magnetically writable disc and at least one write/read head. The hard disc is preferably a removable hard disc which comprises an interface, in particular a galvanic interface with galvanic-electrical contacts, and a portable hard disc storage medium. Exemplary embodiments for an interface of a hard disc of this kind are a USB interface (USB=Universal Serial Bus), an SCSI interface (SCSI=Small Computer System Interface), preferably a WLAN interface (WLAN=Wireless Local Area Network).

In a preferred embodiment the medical system is constructed to compress the data produced by the detection device in such a way and to produce compressed data in such a way that compressed data has a smaller memory space requirement than the data produced by the detection device, and to store the compressed data by means of the storage device. The memory space can advantageously be reduced hereby. For this purpose the medical system can comprise a compression unit which can be implemented at least partially by a central processing unit, in particular a microprocessor. The compression unit can also be part of the storage device.

Exemplary embodiments for a compression unit are an MPEG compression unit (MPEG=Moving Picture Experts Group). An advantageous embodiment for an MPEG compression unit is an MPEG-2 compression unit which is constructed to compress and decompress according to the MPEG-2 standard. In a further advantageous embodiment of the MPEG compression unit it is an MPEG-4 compression unit which, in contrast to an MPEG-2 compression unit, can carry out improved image data compression and improved audio data compression. An MPEG-2 compression unit can operate according to an ISO/IEC13818 standard; an MPEG-4 compression unit can operate according to the ISO/IEC14496 standard.

In a preferred embodiment the medical system is constructed to detect patient data and produce a patient data record which represents the patient data, and the storage device is constructed to receive the patient data record and write on the storage medium in such a way that the storage medium represents the data and the patient data record so it can be read out again. Patient data and patient-related image data, for example an image data stream, which was detected during an operation and includes a series of 2D data records, can thus advantageously be stored together with patient-related data, in particular ASCII data representing data of a patient's file, on a storage medium. In a preferred embodiment the storage device is constructed to produce a hybrid storage medium which can represent data using data formats that are different from each other. The storage device can for example be constructed to produce a storage medium with a data structure according to an ISO9660 standard.

In a preferred embodiment the medical system, in particular the storage device, is constructed to write on a storage medium according to the MPEG-7 standard. Data formats that are different from each other can advantageously be jointly stored and be particularly efficiently compressed on a storage medium by means of an MPEG-7 storage device. For this purpose meta information, which, for example, can be stored on the storage medium in the form of one or more XML document(s), is provided for coding the data, in particular multi-media data.

In an advantageous embodiment a memory location-optimized primary representation of the data can be provided in addition to the meta data. The data can advantageously thus comprise a sequence of 2D data records, a 3D data record, for example representing an object in three dimensions, which has been detected by means of a computer tomograph. In addition to the 2D or 3D data records the medical system can for example also store an audio data record which represents a section of an audio signal over time, for example representing spoken speech. Speech information, for example a dictation, produced by a doctor, can thus advantageously also be stored on the storage medium.

In an advantageous embodiment the medical system comprises at least one image reproduction unit which is actively connected to the medical device, and the medical system being constructed to visibly reproduce the data at least partially by means of the image reproduction unit. Using the at least one image reproduction unit a user, for example a doctor, can, during an operation, observe a 2D data record or a sequence of 2D data records that is to be stored and control storage and/or reproduction of stored data by means of the image reproduction unit. Advantageous embodiments for an image reproduction unit are a TFT display (TFT=Thin Film Transistor) a plasma display or an OLED display (OLED=Organic Light Emitting Diode).

In an advantageous embodiment the medical system comprises an image processing device connected to the storage device and preferably connected to the storage device. The image processing device is constructed to change the 2D data record produced by the detection device and/or the sequence of 2D data records according to at least one predetermined allocation rule, in particular to filter it, and to send a changed 2D data record and/or sequence of changed 2D data records to the storage device for storage. The image processing device can for example comprise a high-pass filter which can filter location-dependent spatial frequencies of a 2D data record and can thus produce a greater image contrast. A further embodiment for a filter for filtering spatial frequencies is a low-pass filter which can advantageously attenuate contrasts in a 2D data record. By way of example the image processing device can comprise an image definition-reducing filter which can reduce a location-dependent image resolution in such a way that 2D data, which represents mutually adjacent pixels, represents the same brightness and/or color value respectively. A location-dependent contrast can thus advantageously be reduced in particular for a region of a 2D data record which represents the face of a patient. The image processing device can also advantageously thus anonymize a 2D data record or sequence of 2D data records.

In an advantageous embodiment the medical system comprises a device for detecting an object in three dimensions and which is constructed to produce a 3D data record. The 3D data record represents an object at least partially in three dimensions and is produced from a plurality of 2D data records which represent the object in a view through the object in detection directions that are different from each other respectively. The 3D data record is preferably produced from the 2D data records by means of back projection, in particular filtered back projection. The medical system is constructed to send the 3D data record at least partially to the storage unit for storage. For example the medical system can produce a data record from a 3D data record which represents a section through the object, a view through an object layer or a plan view of the object or part of the object, and therefore send the 3D data record only partially to the storage unit for storage. Of course the 3D data record can also be completely sent to the storage unit for storage, so after the 3D data record has been read out again a plan view, a through-view or a section through the object can be produced. The medical system can therefore advantageously store image sequences which have been detected during an operation, in particular by means of an x-ray device or a CCD camera, on the storage medium. The medical system can also store patient-related data, for example as an ASCII data record, on the storage medium. The medical system can also preferably store a 3D data record, which, for example, has been produced by means of a magnetic-resonance tomograph or a computer tomograph or an ultrasound detection device, on a storage medium by means of the storage device. The medical system can comprise the magnetic-resonance tomographs, the computer tomograph or the ultrasound detection device or a combination thereof for this purpose.

The invention also relates to a method for storing a 2D data record or a sequence of 2D data records over time in which the 2D data record is a result of a detection of an object by means of x-rays and represents the object in a projection through the object in two dimensions, comprising the steps:
  detecting an object by means of x-rays,
  producing a 2D data record or sequence of 2D data records over time that represents the object,
  digitally transmitting the 2D data record or the sequence of 2D data records over time through to a storage device, and
  optically storing the 2D data record or the sequence of 2D data records over time so it can be read out again on a storage medium by means of the storage device and in particular by means of electromagnetic beams.

The digital transmission of the 2D data record or the sequence of 2D data records over time through to the storage device can in particular be binary, octal or hexadecimal, or a combination thereof. The combination can for example be binary and octal, binary and hexadecimal or octal and hexadecimal.

Further advantageous variants emerge from the features described in the dependent claims or a combination thereof.

BRIEF DESCRIPTION OF THE DRAWINGS

The invention will be described hereinafter with reference to a FIGURE which schematically shows an embodiment for a medical system and further exemplary embodiments.

DETAILED DESCRIPTION OF THE INVENTION

The FIGURE schematically shows an embodiment for a medical system 1. The medical system 1 comprises a medical device 3. In this exemplary embodiment the medical device 3 is an x-ray C-arm device which is constructed to detect an object by means of x-rays in a through-view and to produce a 2D data record or a sequence of 2D data records over time which represent the object in a view through the object respectively. For this purpose the medical device 3 is connected to a CCD detection device 7 (CCD=Charge Coupled Device) and an x-ray image intensifier 8. The medical device 3 is also connected at the input side to a solid-state detector 9 which can be part of the medical device 3. The medical device 3 has an output 5 and is constructed to output the 2D data record or the sequence of 2D data records over time at the output 5.

The medical system 1 also has a processing unit 10, a memory 12 for storing 2D data records, an image processing unit 14, a compression unit 16, an image reproduction unit 18 with a touch-sensitive surface 20, a video interface 22, an image reproduction unit 24, an interface 26, a USB interface 28 (USB=Universal Serial Bus) with an output 30. A USB storage device 32 is connected to the output 30 in this exemplary embodiment. The medical system 1 also comprises a hard disc 31, an optical storage device 34 and an optical reproduction device 35. A storage medium 36, which can be written on by the optical storage device, and the optical storage medium 36 as a writable optical storage medium 36', which can be read from the optical reproduction device 35 is also shown. An optical storage medium 33 is also shown which can be written on by the external storage device 32 and/or read out from again.

The optical storage device 34 and the optical storage device 32 can each be constructed as a DVD storage device, in particular with a laser producing electromagnetic beams for writing on a storage medium in the range between 750 and 800 nanometers, preferably at 780 nanometers. The storage devices 34 and 32 can each be constructed as HD-DVD storage devices which have a laser which can produce electromagnetic laser beams in the range between 380 and 450 nanometers, preferably electromagnetic beams at 405 nanometers.

The image processing unit 14 has an input 17 and is constructed to receive a 3D data record therefrom which represents a detected object in three dimensions. The 3D data records can for example have been produced by a computer tomograph 19 which is connected at the output side to the input 17. As an alternative to the computer tomograph 19 the input 17 can also be connected to a magnetic resonance tomograph and an ultrasound detection device which are each constructed to produce a 3D data record.

The processing unit 10 is connected at the output to a video interface 22 by a connecting line 58. The video interface 22 can for example be a VGA video interface or a SGVA video interface (VGA=Video Graphics Array; SGVA=Super Video Graphics Array) and is connected at the output side to the image reproduction unit 18 by a connecting line 63 and at the output side to the image reproduction unit 24 by a connecting line 61. The touch-sensitive surface 20 of the image reproduction unit 18 is constructed to produce a user interaction signal, as a function of touch—for example by a user's hand 70—which represents a location where the touch-sensitive surface 20 has been touched. The storage interface 26 is connected at the output side to the USB interface 28 by a connecting line 39 and at the output side to the hard disc 31 by a connecting line 49. The connecting lines 39, 47 and 49 can each be constructed as a data bus, in particular as a bi-directional data bus.

The USB interface 28 is connected to the output 30 by a connecting line 43 and the output 30 is detachably connected to the external storage device 32 by a connecting line 45. The optical reproduction device 35 is at least indirectly connected at the output side to the video interface 22 by a connecting line 41. The optical reproduction device 35 can thus read a storage medium 36' located in the optical drive 35 and for example send read-out 2D data records via the connecting line 41 to the video interface 22 for reproduction on the image reproduction unit 18 and/or image reproduction unit 24.

The optical reproduction device 35 and the optical storage device 34 can together form a device, in particular a DVD write-read device. The storage interface 26 is connected at the input side to the processing unit 10 by a bidirectional data bus 51. The processing unit 10 is connected to the compression unit 16 by a connecting line 53 and to the image processing unit 14 by a connecting line 55. The processing unit 10 is also connected to the storage unit 12 by a connecting line 57. The connecting line 57 can also be constructed as a data bus, in particular a bidirectional data bus. The storage unit 12 is constructed for holding in readiness data, in particular 2D data records or a large number of 2D data records which together may form a sequence of 2D data records over time. The 2D data record 13 and the 2D data record 15 are designated therein by way of example. The processing unit 10 is connected at the input side to the touch-sensitive surface 20 by a connecting line 59 and can receive a user interaction signal therefrom via the connecting line 59. The medical device 3 is connected at the output side to the output 5 by a connecting line 65 and at the input side to the CCD detection device 7 by a connecting line 67 and at the input side to the solid-state detector 9 by a connecting line 69. The output 5 is connected to the processing unit 10 by a connecting line 68.

The processing unit 10 can be constructed as a microprocessor, in particular as a microprocessor which can process two or more processes simultaneously. Exemplary embodiments for a microprocessor of this kind are a dual-core microprocessor.

The mode of operation of the medical system 1 will accordingly be described hereinafter:

From the solid-state detector 9 the medical device 3 can receive via the connecting line 69 a 2D data record which for example represents an object, detected by means of x-rays, in a through-view in two dimensions. The solid-state detector 9 can comprise grid matrix elements for this purpose which can each produce a pixel of a two-dimensional image. The grid matrix elements of the solid-state detector 9 can comprise selenium in each case. Via the connecting line 67 the medical device 3 can receive a 2D data record, produced by the CCD detection device, independently of the solid-state detector 9 or in addition to the solid-state detector 9. The CCD detection device can be at least optically connected to the image intensifier 8—shown in broken lines—and receive electromagnetic beams from the image intensifier 8 which together represent a detected object in two dimensions. The image intensifier 8 can be constructed as an x-ray image intensifier and receive x-rays at the input side and intensify these by means of at least one cathode and a faceplate arranged at the output side. A scintillator film, which is preferably connected upstream of an x-ray grid in an x-ray beam path and of which the generated electromagnetic radiation can be detected by the CCD detection device—for example by means of geometrical optics—is also conceivable. The medical device 3 can make the 2D data record produced by means of the CCD detection device 7 and/or the 2D data record produced by means of the solid-state detector 9 or a sequence of 2D data records over time produced in this way available at the output side at the output 5 via the connecting line 65. The sequence of 2D data records over time can for example represent an object, in particular a patient during an operation. The processing unit 10 can receive the 2D data record via the connecting line 68—for example as a function of a user interaction signal produced by the touch-sensitive surface 20 and received via the connecting line 59—and store the received 2D data record in the memory 12 via the connecting line 57. The memory 12 can be constructed as a volatile or non-volatile write-read memory. The processing unit 10 can read the 2D data record or sequence of 2D data records from the memory 12 via the connecting line 57, for example as a function of a user interaction signal received at the input side via the connecting line 59, and send it to the video reproduction interface 22 for reproduction on the image reproduction unit 18 and/or the image reproduction unit 24.

The processing unit 10 can—for example as a function of a user interaction signal received via the connecting line 59—read the sequence of 2D data records from the memory 12 and send it via the bidirectional data bus 51, via the interface unit 24 and via the connecting line 47 to the optical storage device 34 and store it there on the storage medium 36. Direct conveying or forwarding of 2D data records provided at the output 5 via the bidirectional data bus 51, the interface unit 26 and the connecting line 49 to the hard disc 31 in order to store the 2D data records there is also conceivable. The processing unit 10 can also send the 2D data records via the bidirectional data bus 51, the interface unit 26 and the connecting line 39 to the USB interface 28 and from there via the connecting line 43, the output 30 and the connecting line 45 to the external storage device 32 for storage on the storage medium 33.

The hard disc 31 has sufficient storage capacity for storing video sequences, respectively formed by a sequence of 2D data records. A 2D data record received by the processing unit 10 from the output 5 can also be sent via the connecting line 55 to the image processing device 14, before storage on the storage medium 36 or storage medium 33, and be changed there. The image processing device 14 can, for example, change a 2D data record by means of a filter. The filter can be a high-pass, low-pass or band-pass filter which is constructed to filter space-dependent frequencies of a 2D matrix, formed by a 2D data record and comprising matrix elements, according to a predetermined allocation rule. A spatial frequency filter, which forms a high-pass, can for example intensify contrasts of an image or contour lines. A spatial frequency filter, which forms a low-pass, can for example attenuate contrasts or contour lines of an image. A low-pass filter or a spatial frequency-transforming filter, for example for reducing spatial frequencies, can for example be used to anonymize a 2D data record, representing a detection result of a patient. A person-specific feature, for example the face of a patient, can for example thus be rendered unrecognizable. In this exemplary embodiment the image processing unit 14 can also receive a 3D data record via the input 17 and produce a 2D data record therefrom which represents a plan view, a through-view or a section through an object representing the 3D data record. The processing unit 10 can receive the 3D data record or a 2D data record produced therefrom via the connecting line 55 and store it in the memory 12 via the connecting line 57, or send the interface unit 26 to the hard disc 31, the optical storage device 34 or the optical storage device 32 via the bidirectional data bus 51. The processing unit 10 can send a 2D data record or a sequence of 2D data records over time, via the connecting line 53 to the compression unit 16, before storage, and compress it there and receive from the compression unit 16, via the connecting line 53, a compressed 2D data record which corresponds to the 2D data record sent in advance and advantageously requires less memory space. For this purpose the compression unit 16 can be constructed as an MPEG compression unit which can operate according to the MPEG-2, MPEG-4 or MPEG-7 standard. The compression unit 16 can also operate according to the MPEG-1 standard and thus produce a VCD format or an SVCD format of a sequence of 2D data records. Depending on the application, the medical system 1 can thus produce video formats that are different from each other. Production of an AVI video format is also conceivable. The processing unit 10 can also receive person-specific data, for example via the connecting line 68, or produced by the touch-sensitive surface 20, from the medical device 3 and produce a personal data record which represents the person-specific data. Person-specific data can for example be the name of a patient, date of birth of a patient, or the height or weight of a patient. The person-specific data can also be in the form of a report about a state of health of a patient, in particular in text form, for example in ASCII format or in spoken form, and exist for example as a dictation in a wave format. A person-specific data record, representing spoken speech, can for example be produced by a speech input unit 25 which is connected at the output side to the processing unit 10 via a connecting line 56. The speech input unit 25 can comprise a microphone and can be constructed to receive airborne noise representing speech and to produce a speech data record which represents the airborne noise. The processing unit 10 can compress the speech data record, the personal data record, a 2D data record produced by the image processing unit 14, a 2D data record produced by the medical device 3 or a sequence of 2D data records, by means of the compression unit 16 according to a predetermined data format to produce a compression data record and send the compressed data record via the connecting line 51 to the storage interface 26 for storage on an optical storage medium for example the storage medium 36 or storage medium 33. The compressed data format for compressing data that is different, comprising image data, speech data and text data, can advantageously be an MPEG-7 format. The data can thus be stored losslessly on a storage medium and when read out again from the storage medium—for example by means of the optical reproduction device 35 or optical storage device 32—be reproduced in a high quality.

The invention claimed is:

1. A medical system, comprising:
   a detection device that detects an object in at least two dimensions and outputs a data record of the object;
   a storage device actively connected to the detection device that receives the data record and writes the data records on a storage medium of the storage device, the data record being digitally transmitted from the detection device to the storage device; and
   an imaging processing device connected to the storage device that changes the data record according to a predetermined allocation rule and the changed data record is saved on the storage device,
   wherein the imaging processing device comprises:
      a high-pass filter that filters location-dependent spatial frequencies of the data record for intensifying an image contrast of the data record, and
      a low-pass filter that filters the location-dependent spatial frequencies of the data record for attenuating the image contrast of the data record,
      an image definition filter that filters the location-dependent spatial frequencies of the data record for reducing a location-dependent image resolution of the data record so that mutually adjacent pixels of the data record represents a same brightness and/or color value respectively,
   wherein the detection device is configured to digitally transmit the data record to the storage device in a combination of binary, octal, or hexadecimal comprising binary and octal, binary and hexadecimal, or octal and hexadecimal, and
   wherein the storage medium comprises at least two storage layers arranged parallel to each other.

2. The medical system as claimed in claim 1, wherein the storage device is an optical storage device and writes the data record on the storage medium by electromagnetic beams.

3. The medical system as claimed in claim 1, wherein the storage device is a magneto-optical storage device and magnetically writes the data record on the storage medium.

4. The medical system as claimed in claim 1, wherein the storage device is a magnetic storage device producing a magnetic field and writes the data record on the storage medium by the magnetic field.

5. The medical system as claimed in claim 1, wherein the medical system detects a patient data record comprising a personal data record of a patient that is transmitted from the detection device to the storage device for reading out again.

6. The medical system as claimed in claim 1, wherein the medical system compresses the data record and the compressed data record is saved on the storage.

7. The medical system as claimed in claim 1, wherein the medical system comprises an image reproduction unit that visibly reproduces the data record.

8. The medical system as claimed in claim 1, wherein the data record is detected by x-rays.

9. The medical system as claimed in claim 1, wherein the data record is a 2D data record or a sequence of 2D data records over time.

10. The medical system as claimed in claim 1, wherein a 3D data record of the object is generated from a plurality of 2D data records and is digitally transmitted to the storage device for storage.

11. A method for storing a data record of an object, comprising:
    generating the data record of the object by detecting the object;
    digitally transmitting the data record to a storage device;
    optically storing the data record on a storage medium of the storage device for reading out the data record again;
    changing the data record according to a predetermined allocation rule; and
    storing the changed data record on the storage medium of the storage device for reading out the changed data record again,
    wherein the data record is changed according to the predetermined allocation rule by:
       filtering location-dependent spatial frequencies of the data record by a high-pass filter for intensifying an image contrast of the data record,
       filtering the location-dependent spatial frequencies of the data record by a low-pass filter for attenuating the image contrast of the data record,
       filtering the location-dependent spatial frequencies of the data record by an image definition filter for reducing a location-dependent image resolution of the data record so that mutually adjacent pixels of the data record represents a same brightness and/or color value respectively,
    wherein the data record is digitally transmit to the storage device in a combination of binary, octal, or hexadecimal comprising binary and octal, binary and hexadecimal, or octal and hexadecimal, and
    wherein the storage medium comprises at least two storage layers arranged parallel to each other.

12. The method as claimed in claim 11, wherein the storage device is an optical storage device and writes the data record on the storage medium by electromagnetic beams.

13. The method as claimed in claim 11, wherein the storage device is a magneto-optical storage device and magnetically writes the data record on the storage medium.

14. The method as claimed in claim 11, wherein the storage device is a magnetic storage device producing a magnetic field and writes the data record on the storage medium by the magnetic field.

15. The method as claimed in claim 11, wherein the data record is detected by x-rays.

16. The method as claimed in claim 11, wherein the data record is a 2D data record or a sequence of 2D data records over time.

* * * * *